US009421312B1

(12) United States Patent
Marinan et al.

(10) Patent No.: US 9,421,312 B1
(45) Date of Patent: Aug. 23, 2016

(54) MODULAR CHASE SYSTEMS (71) Applicant: PERMACHASE CORPORATION, Merriam, KS (US)

(72) Inventors: Kevin J. Marinan, Scottsdale, AZ (US); Jack R. Dillon, Leawood, KS (US); Matthew C. Lamont, Glendale, AZ (US)

(73) Assignee: MARATHON RESOURCES, INC., Mesa, AZ (US)

( * ) Notice: Subject to any disclaimer, the term of this patent is extended or adjusted under 35 U.S.C. 154(b) by 468 days.

(21) Appl. No.: 13/872,902

(22) Filed: Apr. 29, 2013

Related U.S. Application Data

(60) Provisional application No. 61/641,148, filed on May 1, 2012, provisional application No. 61/658,871, filed on Jun. 12, 2012.

(51) Int. Cl.
| *B01D 61/30* | (2006.01) |
| *A61M 1/14* | (2006.01) |
| *A47B 81/00* | (2006.01) |
| *A47B 96/00* | (2006.01) |
| *E03C 1/02* | (2006.01) |
| *E03B 7/09* | (2006.01) |
| *A47B 96/20* | (2006.01) |

(52) U.S. Cl.
CPC ............... *A61M 1/14* (2013.01); *A47B 81/00* (2013.01); *A47B 96/205* (2013.01); *E03B 7/095* (2013.01); *E03C 1/021* (2013.01); *A61M 2209/08* (2013.01)

(58) Field of Classification Search
CPC ........ B01D 61/30; A61M 1/14; A61M 1/16; A61M 1/1621; A61M 2209/00; A61M 2209/08; A61M 2209/082; A61M 2209/084; A61M 2209/086; F16L 3/00; F16L 5/00; F16L 41/00; F16L 41/04; F16L 41/045; A47B 57/00; A47B 81/00; A47B 96/00; A47B 96/04; A47B 96/06; A47B 96/20; A47B 96/205; A47B 2096/208; A47B 97/00; E03C 1/02; E03C 1/021; E03C 1/025; E03B 5/02; E03B 7/04; E03B 7/07; E03B 7/08; E03B 7/09; E03B 7/095
USPC ........................ 210/321.6, 321.71, 541, 646; 137/315.01, 343, 356, 357, 360, 362; 52/27, 36.4, 36.5, 220.1, 220.3, 220.7, 52/220.8; 211/85.13, 87.01, 94.01, 96; 312/242, 245, 351.1; D24/169, 185
See application file for complete search history.

(56) References Cited

U.S. PATENT DOCUMENTS

| | | | |
|---|---|---|---|
| 3,148,698 A | | 9/1964 | Arnold |
| 4,589,557 A | * | 5/1986 | Bollmann .................. 211/94.01 |
| 4,641,468 A | * | 2/1987 | Slater ............................ 52/309.4 |
| 4,646,211 A | | 2/1987 | Gallant et al. |
| 6,197,197 B1 | | 3/2001 | Peterson et al. |
| 6,581,627 B2 | | 6/2003 | Dillon |
| D484,599 S | * | 12/2003 | Kellar .......................... D24/169 |
| 7,174,678 B2 | * | 2/2007 | Gallant .......................... 52/36.1 |
| 8,441,782 B2 | * | 5/2013 | Thomas .................... 361/679.02 |
| 8,834,718 B2 | * | 9/2014 | Randall et al. .......... 210/321.71 |
| 2002/0174483 A1 | * | 11/2002 | Gallant ..................... A61G 7/00 4/664 |
| 2010/0095604 A1 | * | 4/2010 | Newkirk et al. ............... 52/79.1 |
| 2011/0115351 A1 | | 5/2011 | McManic et al. |
| 2011/0219706 A1 | * | 9/2011 | Bates et al. .................... 52/36.1 |

* cited by examiner

*Primary Examiner* — Joseph Drodge
(74) *Attorney, Agent, or Firm* — Tod R. Nissle, P.C.

(57) ABSTRACT

A modular wall-chase system relating to the routing of mechanical elements (plumbing, electrical, data, etc.) within the interior of a new, or already built, structure and particularly relating to the interior of a kidney-dialysis treatment facility.

1 Claim, 11 Drawing Sheets

MODULAR CHASE SYSTEMS

CROSS-REFERENCE TO RELATED APPLICATION

The present application is related to and claims priority from prior provisional application Ser. No. 61/641,148, filed May 1, 2012, entitled "MODULAR CHASE SYSTEMS"; and, this application is related to and claims priority from prior provisional application Ser. No. 61/658,871, filed Jun. 12, 2012, entitled "MODULAR CHASE SYSTEMS", the contents of all of which are incorporated herein by this reference and are not admitted to be prior art with respect to the present invention by the mention in this cross-reference section.

BACKGROUND

This invention relates to providing systems for improved modular wall chase(s). More particularly, this invention relates to providing a modular wall-chase system for the routing of mechanical (plumbing, electrical, data, etc.) elements within the interior of a built structure, particularly within the interior of a specialty medical facility.

Present-day kidney-dialysis machines commonly require an external source of treated water, acid and bicarbonate concentrates dialysate, electrical power, etc., in addition to a means for waste-fluid disposal. Many contemporary kidney-dialysis clinics employ groupings of multiple kidney-dialysis machines, each typically located within a common interior treatment room. Clearly, an improved means for efficiently and conveniently supplying mechanical, electrical, and plumbing to multiple groupings of dialysis units would reduce the cost of delivery and operation of contemporary kidney-dialysis clinics.

OBJECTS AND FEATURES OF THE INVENTION

A primary object and feature of the present invention is to provide a system addressing the above-mentioned need(s). It is a further object and feature of the present invention to provide such a system providing a set of modular chase components configured to be quickly and easily site assembled to for an operable mechanical chase within the interior of a built structure. Another object and feature of the present invention to provide such a system providing a means for protectively containing plumbing valves and connections to minimize damage should a leak occur. A further object and feature of the present invention to provide such a system providing multifunctional components capable of being adapted to many particular project design requirements. A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a dialysis support system, relating to consolidating local building services associated with the operation of at least one hemodialysis machine within at least one treatment facility, such dialysis support system comprising: at least one first consolidator panel structured and arranged to consolidate at least a set of fluid-transfer elements of the local building services; wherein such at least one first consolidator panel comprises at least one removable mount structured and arranged to assist removable mounting of such at least one first consolidator panel to at least one surface of the at least one treatment facility, at least one fluid collector structured and arranged to collect at least one discharged fluid, at least one connection positioner structured and arranged to position, in a fluid-collecting arrangement with respect to such at least one fluid collector, at least three termination connections of the first set of fluid-transfer elements, and at least one termination-connection access structured and arranged to enable physical access to each one of the at least three termination connections without repositioning of such at least one consolidator panel from at least one mounted position with respect to such at least one surface; and wherein, when assembled for use, such at least one fluid collector assists capture of fluids discharged from any one of the at least three termination connections.

Moreover, it provides such a dialysis support system wherein such at least one fluid collector comprises at least one fluid-drain coupler structured and arranged to assist coupling of such at least one fluid collector to at least one fluid-drain element of the local building services. Additionally, it provides such a dialysis support system further comprising: at least one second consolidator panel structured and arranged to consolidate at least a set of electrical-supply elements of the local building services; wherein such at least one second consolidator panel comprises such at least one removable mount structured and arranged to assist removable mounting of such at least one second consolidator panel to the at least one surface of the at least one treatment facility; and wherein such at least one second consolidator panel is further structured and arranged to physically conform to at least one modularized format.

Also, it provides such a dialysis support system wherein such at least one first consolidator panel is further structured and arranged to physically conform to the at least one modularized format. In addition, it provides such a dialysis support system wherein such at least one first consolidator panel substantially comprises at least one polymer; The dialysis support system wherein such at least one second consolidator panel substantially comprises at least one polymer, and wherein such at least one first consolidator panel comprises: a generally rectilinear peripheral shape having at least one top edge and at least one bottom edge spaced apart from and substantially parallel to such at least one top edge, at least one first side edge and at least one second side edge spaced apart from and substantially parallel to such at least one first side edge; a maximum height extending between such at least one top edge and such at least one bottom edge of about 32 inches; and a maximum width extending between such at least one first side edge and such at least one second side edge of about 24 inches.

And, it provides such a dialysis support system wherein such at least one second consolidator panel comprises: a generally rectilinear peripheral shape having at least one top edge and at least one bottom edge spaced apart from and substantially parallel to such at least one top edge, at least one first side edge and at least one second side edge spaced apart from and substantially parallel to such at least one first side edge; a maximum height extending between such at least one top edge and such at least one bottom edge of about 32 inches; and a maximum width extending between such at least one first side edge and such at least one second side edge of about 24 inches.

Further, it provides such a dialysis support system wherein such at least one second consolidator panel comprises: a generally rectilinear peripheral shape having at least one top edge and at least one bottom edge spaced apart from and substantially parallel to such at least one top edge, at least one first side edge and at least one second side edge spaced apart from and substantially parallel to such at least one first side edge; a maximum height extending between such at least one top edge and such at least one bottom edge of about 32 inches; and a maximum width extending between such at least one first side edge and such at least one second side edge of about 24 inches.

Even further, it provides such a dialysis support system further comprising: at least one at least partially prefabricated support frame; wherein at least one portion of such at least one at least partially prefabricated support frame comprises such at least one surface; and wherein such at least one at least partially prefabricated support frame is structured and arrange to support at least one of such at least one first consolidator panel and such at least one second consolidator panel, and assist at least partially-concealed routing of at least one member of the set of fluid-transfer elements and the set of electrical-supply elements. Moreover, it provides such a dialysis support system wherein such at least one removable mount further comprises: at least one releasable coupler structured and arranged to releasably couple a respective one of such at least one first consolidator panel and such at least one second consolidator panel to such at least one portion of such at least one support frame; wherein such at least one releasable coupler is hand operable without the use of tools. And, it provides such a dialysis support system wherein such at least one removable mount further comprises plumbing-connection coverer means for removably covering the at least one plumbing-supply connection located within such fluid-leak capturer means.

Additionally, it provides such a dialysis support system wherein such at least one first consolidator panel further comprises: at least one termination-connection cover structured and arranged to be positionable to at least partially cover the at least three termination connections when the at least three termination connections are positioned in the fluid-collecting arrangement with respect to such at least one fluid collector; wherein such at least one termination-connection cover comprises at least one releasable retainer structured and arranged to releasably retain such at least one termination-connection cover in the position at least partially covering the at least three termination connections. Also, it provides such a dialysis support system wherein such at least one releasable retainer comprises at least one magnetic retainer structured and arranged to magnetically retain such at least one termination-connection cover in the position at least partially covering the at least three termination connections.

In addition, it provides such a dialysis support system wherein such at least one releasable retainer comprises at least one pivot retainer structured and arranged to pivotally retain such termination-connection cover with such at least one first consolidator panel. And, it provides such a dialysis support system further comprising, mountable to at least one portion of such at least one at least partially prefabricated support frame, at least one upper surface structured and arranged to provide at least partial upper surface covering of such at least one at least partially prefabricated support frame.

In accordance with another preferred embodiment hereof, this invention provides a modularized dialysis-chase assembly system assisting modularized assembly, within at least one treatment facility, of at least one dialysis-services chase that, when assembled, provides at least partially concealed routing of local building services associated with the operation of at least one hemodialysis machine, such dialysis support system comprising: at least one first consolidator panel structured and arranged to consolidate at least a set of fluid-transfer elements of the local building services; at least one at least partially prefabricated support frame structured and arrange to support at least one portion of at least one of such at least one first consolidator panel and such at least one second consolidator panel; and mountable to at least one portion of such at least one at least partially prefabricated support frame, at least one upper surface structured and arranged to provide at least partial upper surface covering of such at least one at least partially prefabricated support frame; wherein such at least one first consolidator panel comprises at least one removable mount structured and arranged to assist removable mounting of such at least one first consolidator panel to at least one surface of at least one at least partially prefabricated support frame, at least one fluid collector structured and arranged to collect at least one discharged fluid, at least one connection positioner structured and arranged to position, in a fluid-collecting arrangement with respect to such at least one fluid collector, at least three termination connections of the first set of fluid-transfer elements, and at least one termination-connection access structured and arranged to enable physical access to each one of the at least three termination connections without repositioning of such at least one consolidator panel from at least one mounted position with respect to such at least one at least partially prefabricated support frame; wherein, when assembled for use, such at least one fluid collector assists capture of fluids discharged from any one of the at least three termination connections; and wherein modularized assembly of such at least one dialysis-services chase, providing at least partially concealed routing of the local building services associated with the operation of the at least one hemodialysis machine, is assisted.

Further, it provides such a modularized dialysis-chase assembly system wherein such at least one fluid collector comprises at least one fluid-drain coupler structured and arranged to assist coupling of such at least one fluid collector to at least one fluid-drain element of the local building services. Even further, it provides such a modularized dialysis-chase assembly system further comprising: at least one second consolidator panel structured and arranged to consolidate at least a set of electrical-supply elements of the local building services; wherein such at least one second consolidator panel comprises such at least one removable mount structured and arranged to assist removable mounting of such at least one second consolidator panel to the at least one surface of the at least one treatment facility; and wherein such at least one second consolidator panel is further structured and arranged to physically conform to at least one modularized format.

Moreover, it provides such a modularized dialysis-chase assembly system wherein such at least one first consolidator panel is further structured and arranged to physically conform to the at least one modularized format. Additionally, it provides such a modularized dialysis-chase assembly system wherein such at least one first consolidator panel and such at least one second consolidator panel substantially comprise at least one polymer. Also, it provides such a modularized dialysis-chase assembly system wherein such at least one first consolidator panel and such at least one second consolidator panel each comprise: a generally rectilinear peripheral shape having at least one top edge and at least one bottom edge spaced apart from and substantially parallel to such at least one top edge, at least one first side edge and at least one second side edge spaced apart from and substantially parallel to such at least one first side edge; a maximum height extending between such at least one top edge and such at least one bottom edge of about 32 inches; and a maximum width extending between such at least one first side edge and such at least one second side edge of about 24 inches.

In accordance with another preferred embodiment hereof, this invention provides a dialysis support system, relating to consolidating local building services associated with the operation of at least one hemodialysis machine within at least one treatment facility, such dialysis support system comprising: first consolidating means for consolidating at least a set of fluid-transfer elements of the local building services; wherein such first consolidating means comprises removable mounting means for assisting removable mounting of such first consolidating means to at least one surface of the at least one treatment facility, fluid collecting means for collecting at least one discharged fluid, connection positioning means for positioning, in a fluid-collecting position with respect to such fluid collecting means, at least three termination connections of the first set of fluid-transfer elements, termination-connection accessing means for enabling physical access to each one of the at least three termination connections without repositioning of such consolidating means from at least one mounted position with respect to such at least one surface; and wherein, when assembled for use, such fluid collecting means assists capture of fluids discharged from any one of the at least three termination connections. In addition, it provides such a dialysis support system further comprising second consolidating means for consolidating at least a set of electrical-supply elements of the local building services.

In accordance with another preferred embodiment hereof, this invention provides a method of assembling, within at least one treatment facility, at least one dialysis-services chase that, when assembled, provides at least partially concealed routing of local building services associated with the operation of at least one hemodialysis machine, such method comprising the steps of: providing at least one first consolidator panel structured and arranged to consolidate at least a set of fluid-transfer elements of the local building services; providing at least one at least partially prefabricated support frame structured and arrange to support such at least one first consolidator panel, and assist at least partially-concealed routing of at least one member of the set of fluid-transfer elements; providing, mountable to at least one portion of such at least one at least partially prefabricated support frame, at least one upper surface structured and arranged to provide at least partial upper surface covering of such at least one at least partially prefabricated support frame; and assembling to such at least one at least partially prefabricated support frame, such at least one first consolidator panel, and such at least one upper surface; wherein such at least one first consolidator panel comprises at least one removable mount structured and arranged to assist removable mounting of such at least one first consolidator panel to at least one surface of at least one at least partially prefabricated support frame, at least one fluid collector structured and arranged to collect at least one discharged fluid, at least one connection positioner structured and arranged to position, in a fluid-collecting arrangement with respect to such at least one fluid collector, at least three termination connections of the first set of fluid-transfer elements, and at least one termination-connection access structured and arranged to enable physical access to each one of the at least three termination connections without repositioning of such at least one consolidator panel from at least one mounted position with respect to such at least one at least partially prefabricated support frame; wherein, when assembled for use, such at least one fluid collector assists capture of fluids discharged from any one of the at least three termination connections; and wherein modularized assembly of such at least one dialysis-services chase, providing at least partially concealed routing of the local building services associated with the operation of the at least one hemodialysis machine, is assisted. And, it provides such a method further comprising the step of providing at least one second consolidator panel structured and arranged to consolidate at least a set of electrical-supply elements of the local building services.

In accordance with a preferred embodiment hereof, this invention provides each and every novel feature, element, combination, step and/or method disclosed or suggested by this patent application.

DETAILED DESCRIPTION OF THE BEST MODES AND PREFERRED EMBODIMENTS OF THE INVENTION

Figure 1:
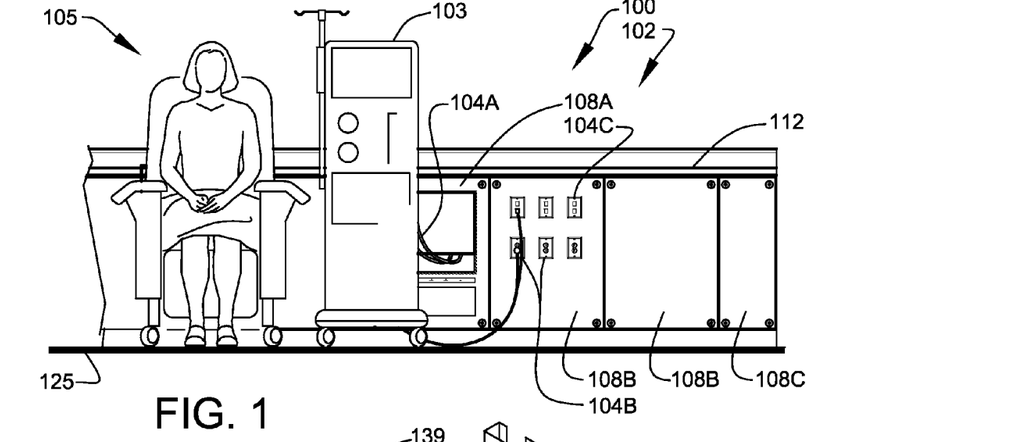
FIG. 1 shows front elevational view, illustrating a modular wall-chase, of a modular wall-chase system, for the routing of mechanical (plumbing, electrical, data, etc.) elements within the interior of a kidney dialysis facility, according to a preferred embodiment of the present invention.
Figure 2:
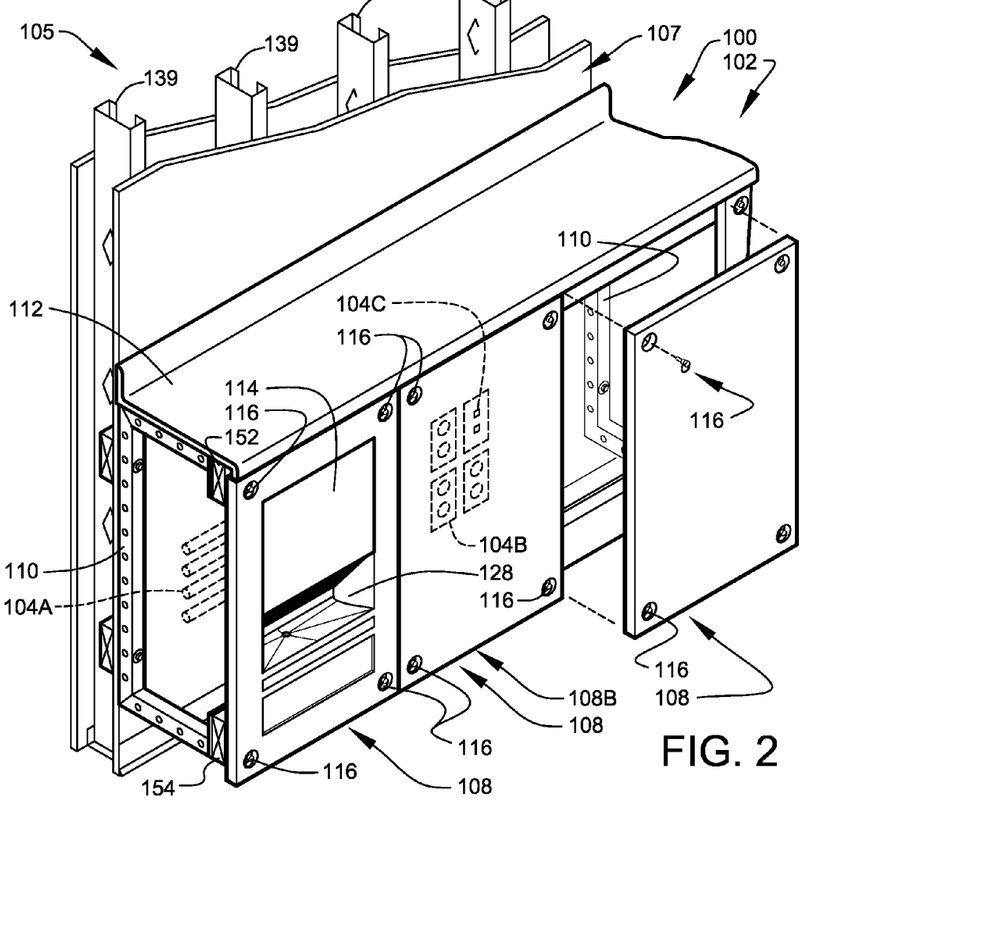
FIG. 2 shows a partially-exploded perspective view, in partial section, illustrating preferred component arrangements of the modular wall-chase, according to the preferred embodiment of FIG. 1.

Referring to the accompanying illustrations, FIG. 1 shows a front elevational view, illustrating an assembled modular wall-chase 102, of modular-component chase system 100. FIG. 2 shows a partially-exploded perspective view, in partial section, illustrating preferred component arrangements of modular wall-chase 102, according to the preferred embodiment of FIG. 1.

The preferred embodiments of modular-component chase system 100 preferably function to provide at least partially concealed routing of a broad spectrum of both common and specialty service elements 104 within specialized medical facilities. The present system is especially useful in the construction and operation of the type of kidney dialysis facilities 105 depicted in FIG. 1. The types of local building service elements which may be supported within modular wall-chase 102 generally include fluid-transfer elements 104A (i.e., plumbing lines), electrical-supply elements 104B, and data elements 104C, as shown. Modular wall-chase 102 is preferably designed to enable efficient installation and maintenance of such building services and, once assembled, provides superior operational support of the kidney-dialysis machines 103 depicted in FIG. 1. In the present disclosure, the term local building services shall be generally defined to at least include plumbing lines (both supply and waste), plumbing fittings, plumbing equipment, electrical lines, electrical equipment (outlets, circuit breakers, transformers, etc.), data lines, and data-related equipment (data outlets, sensors, security components, etc.)

The present system permits cost-effective implementation of the required dialysis-support improvements to an existing building interior, preferably without having to re-build existing walls 107 of the building structure. In new building construction, the present system permits rapid installation of support chases required for the operation of the kidney-dialysis machines 103. In both new and existing construction, the overall in-service performance of the building is improved.

Figure 3:
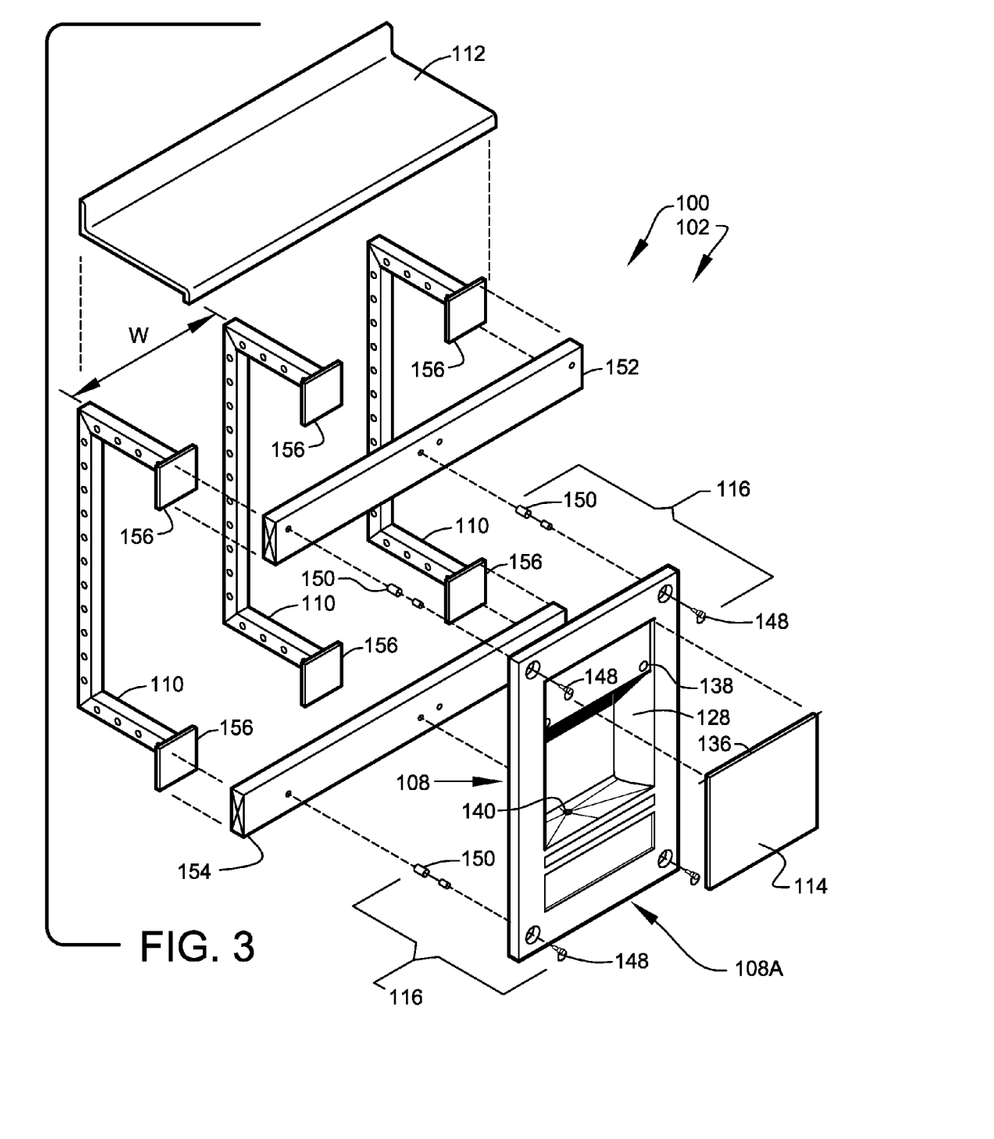
FIG. 3 shows an exploded perspective view, further illustrating preferred component arrangements of the modular wall-chase, according to the preferred embodiment of FIG. 1.

FIG. 3 shows an exploded perspective view, further illustrating preferred component arrangements of modular wall-chase 102, according to the preferred embodiment of FIG. 1. Referring to FIG. 1 through FIG. 3, preferred components of the preferred embodiments of modular-component chase system 100 include a set of preformed consolidator panels 108, partially preassembled support frames 110, and finishing millwork top 112.

Preferably, a majority of the support frames 110 are at least partially preassembled off-site and are preferably designed to be quickly mountable to a wall 107 and/or floor surface 125 of kidney dialysis facility 105 after delivery to the building site. Once mounted, the generally C-shaped support frames 110 preferably define a chase region within which the required service elements 104 (that is, the support and routing of fluid-transfer elements 104A, electrical-supply elements 104B, data elements 104C, etc.) are routed, as diagrammatically shown in FIG. 2. Support frames 110 are preferably configured to support the mounting of one or more of the preformed consolidator panels 108, in addition to the upper millwork top 112, as shown in FIG. 1 and FIG. 2.

Support frames 110 are preferably fabricated from one or more rigid materials capable of forming a rigid structural support member. Support frames 110 are preferably constructed from mild steel channels, as shown, which are preferably joined into the preferred C-shaped configuration by thermal welding, or other known means for joining such metallic members (i.e., brackets in combination with mechanical fasteners).

Preferred support-frame materials are relatively water resistant or, alternately preferably, such support-frame materials are finished in one or more water-resistant coatings. The channel framing is most preferably finished in a protective coating with a powder coated finish being most preferred. Steel channel products suitable for use in the construction of support frames 110 preferably include products sold under the Uni-strut® brand name. Upon reading this specification, those with ordinary skill in the art will now appreciate that, under appropriate circumstances, considering such issues as design preference, user preferences, marketing preferences, cost, structural requirements, available materials, technological advances, etc., other framing member arrangements such as, for example, the use of standard mild-steel mill shapes, the use of alloy extrusions, etc., may suffice.

Alternately preferably, support frames 110 are constructed from a synthetic composite lumber product, such as, for example, a composite wood material consisting of recycled plastic and reclaimed wood. Synthetic composite lumber products suitable for use in the construction of support frames 110 preferably include products conforming to ASTM D 7031-04 standard specification for evaluating mechanical and physical properties of wood-plastic composite products.

Figure 4:
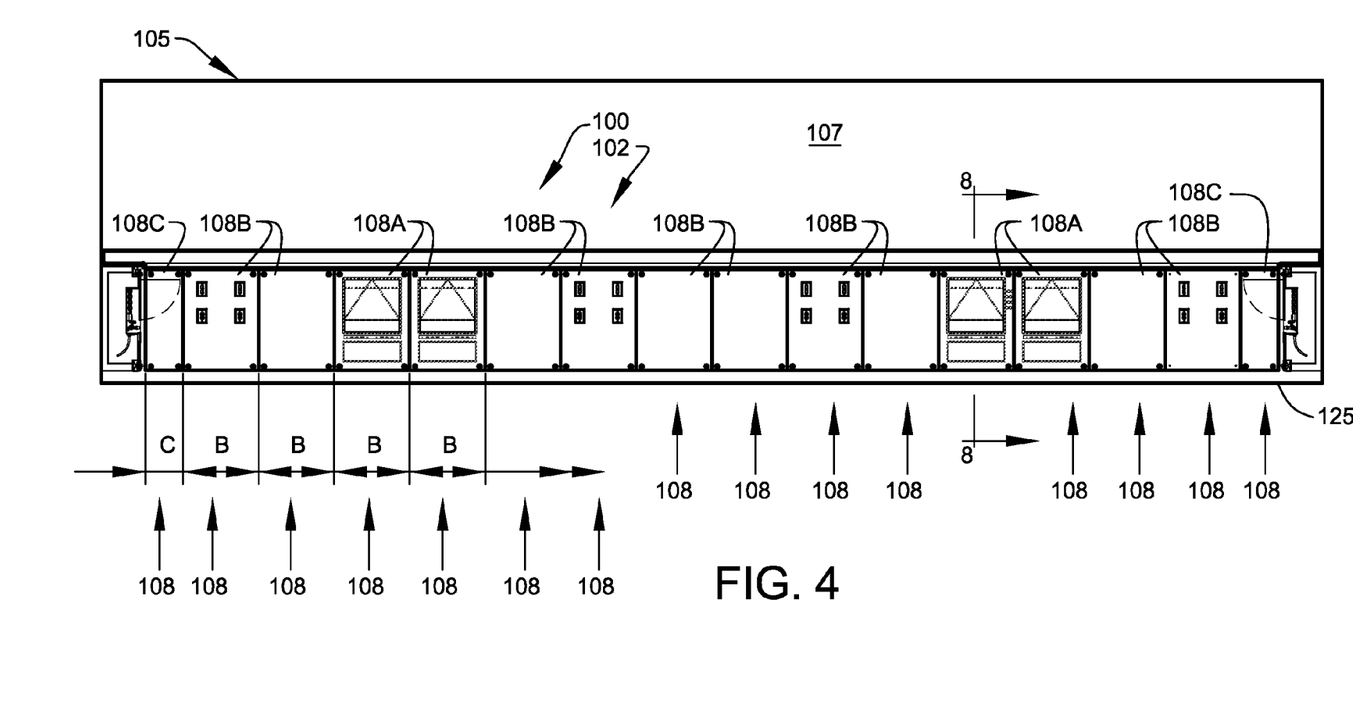
FIG. 4 shows a front elevational view, showing one example of a preferred installation of the modular wall-chase of FIG. 1.

FIG. 4 shows a front elevational view, showing one example of a preferred installation of modular wall chase 102 of FIG. 1. The basic system embodiments preferably comprise at least two types of preformed consolidator panels 108, as shown. The first panel type (see also FIG. 5) preferably comprises plumbing consolidation panel 108A, which preferably functions to secure and support fluid-transfer elements (plumbing components) associated with the operation of kidney-dialysis machine 103. The second preferred panel type comprises multipurpose panel 108B (see also FIG. 13 and FIG. 14), which is most preferably used either as a blank cover for portions of the underlying support frame 110 or as a means for consolidating and supporting electrical-supply elements 104B and data elements 104C, as shown in FIG. 1, FIG. 2, and FIG. 4.

Figure 5:
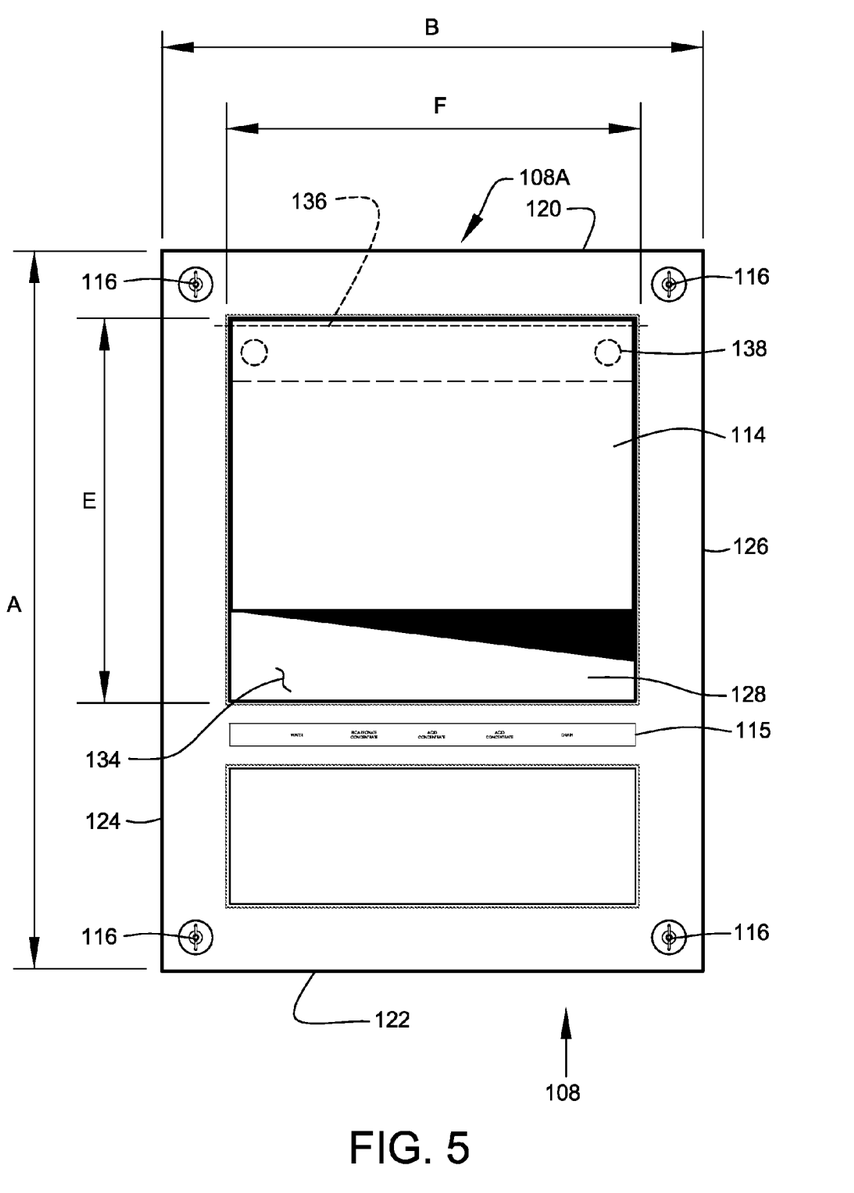
FIG. 5 shows a front elevational view, illustrating a plumbing consolidation panel, according to the preferred embodiment of FIG. 1.
Figures 13, 14:
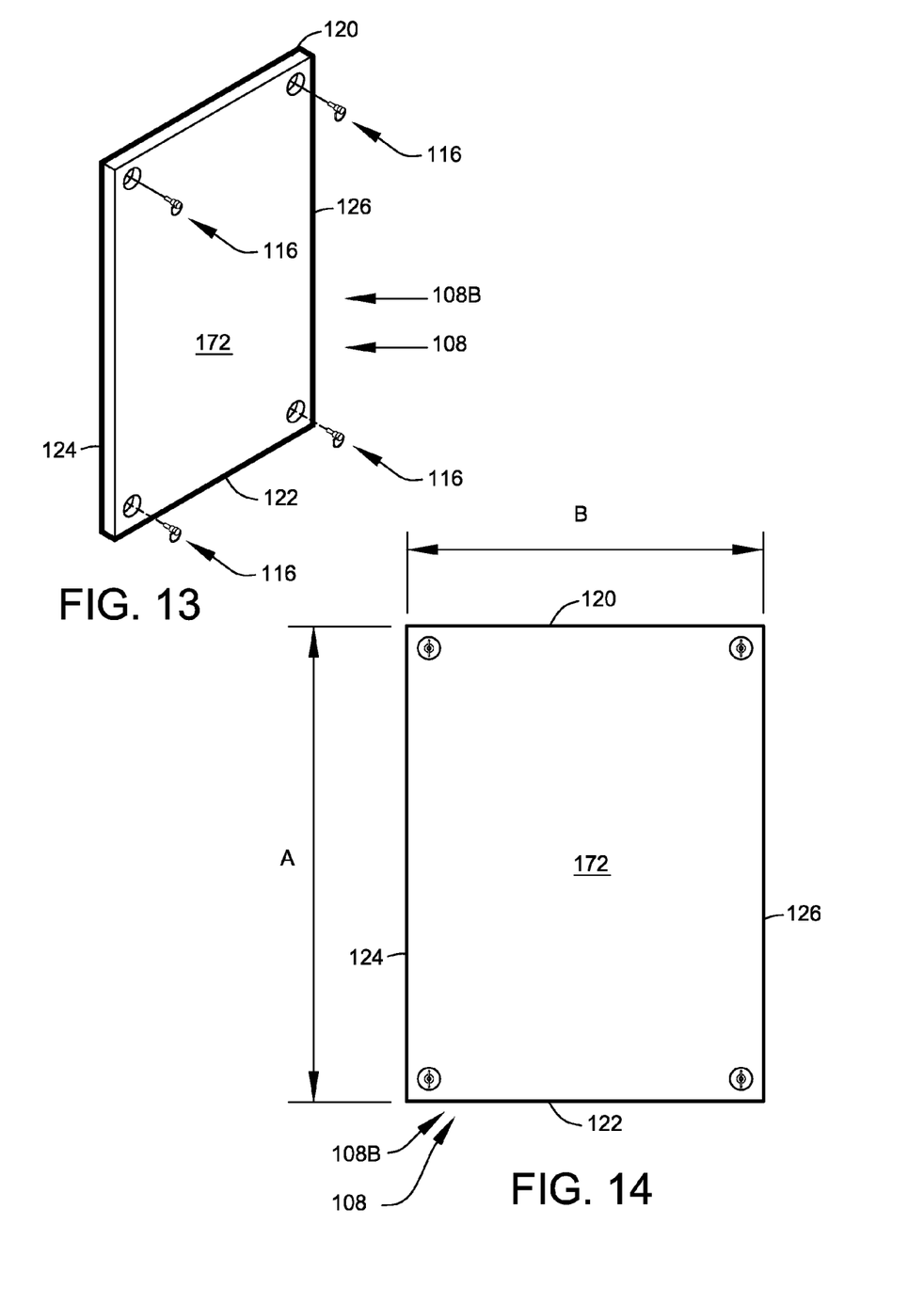
FIG. 13 shows a perspective view, illustrating a multi-functional consolidation panel, according to the preferred embodiment of FIG. 1.
FIG. 14 shows a front elevational view, further illustrating the multi-functional consolidation panel of FIG. 13.

Each standard consolidator panel 108 preferably comprises a generally rectilinear peripheral shape having a top edge 120 and a bottom edge 122 spaced apart from and substantially parallel to top edge 120. In addition, each standard consolidator panel 108 preferably comprises a first side edge 124 and a second side edge 126 spaced apart from and substantially parallel to such first side edge 124, as shown in FIG. 5 and FIG. 14.

Preferably, consolidator panels 108 are structured and arranged to physically conform to at least one modularized size format. In more specific terms, each standard-sized consolidator panel 108 preferably comprises a maximum height A, extending between top edge 120 and bottom edge 122, of about 32 inches. Each standard-size consolidator panel 108 preferably comprises a maximum width B, extending between first side edge 124 and second side edge 126, of about 24 inches. To better accommodate existing and non-modular room dimensions, modular-component chase system 100 may also preferably comprise panels of half-module width C, as shown in FIG. 4. Upon reading this specification, those with ordinary skill in the art will now appreciate that, under appropriate circumstances, considering such issues as design preference, building configuration, cost, structural requirements, etc., other panel arrangements such as, for example, panels that are non-modular in size, panels that may be cut-to-fit, etc., may suffice.

Each consolidator panel 108 is preferably constructed from at least one wear-resistant and water-resistant material capable of providing a readily sanitizable surface. Consolidator panels 108 are preferably constructed from at least one thermo-formable polymer, preferably an acrylic-polyvinyl chloride thermoplastic polymer. Preferred acrylic-polyvinyl chloride thermoplastic polymers are preferably formulated to comprise a Rockwell "R" scale hardness of about 90. Acrylic-polyvinyl chloride thermoplastic polymers suitable for use in the formation of consolidator panels 108 include products distributed under the KYDEX® brand by KYDEX, LLC of Bloomsburg, Pa. (at least embodying herein wherein such at least one first consolidator panel substantially comprises at least one polymer and wherein such at least one second consolidator panel substantially comprises at least one polymer). Upon reading this specification, those with ordinary skill in the art will now appreciate that, under appropriate circumstances, considering such issues as design preference, user preferences, marketing preferences, cost, structural requirements, available materials, technological advances, etc., other material arrangements such as, for example, the use of alternate polymers (ABS, PVC, HDPE, LDPE, etc.), the use of metallic materials (aluminum, stainless steel, etc.), the use of composites, etc., may suffice.

As shown in FIG. 3 and FIG. 4, a modular wall-chase 102 supporting the operation of multiple kidney-dialysis machines 103 may be developed by mounting a series of consolidator panels 108 over two or more installed support frames 110. Support frames 110 are preferably installed at an interval W of about two feet. Interval W preferably corresponds generally to the preferred module of the preformed panels. As the preformed panels and support frames of modular-component chase system 100 are preferably modular, dialysis-support chases of many configurations may be developed to best match the design requirements of a particular kidney-dialysis facility 105.

Plumbing consolidation panel 108A is preferably configured to be mounted to and cover a portion of the partially preassembled support frames 110, as shown. Plumbing consolidation panel 108A is preferably mounted using a set of removable quick-release fasteners 116, which preferably assist the quick mounting and demounting of the panel to/from support frame 110. This preferred feature assists modification, inspection, and repair procedures by permitting convenient access to service elements 104 located within the chase.

Plumbing consolidation panel 108A preferably comprises at least one integrally-formed fluid collector 128 configured to collect at least one discharged fluid produced during the operation of the facility. Fluid collector 128 preferably comprises a region, recessed within the outer face of the panel, having a preferred width D of about 18 inches, a preferred height E of about 23 inches, and a preferred depth F of about 3½ inches.

Figures 6, 7:
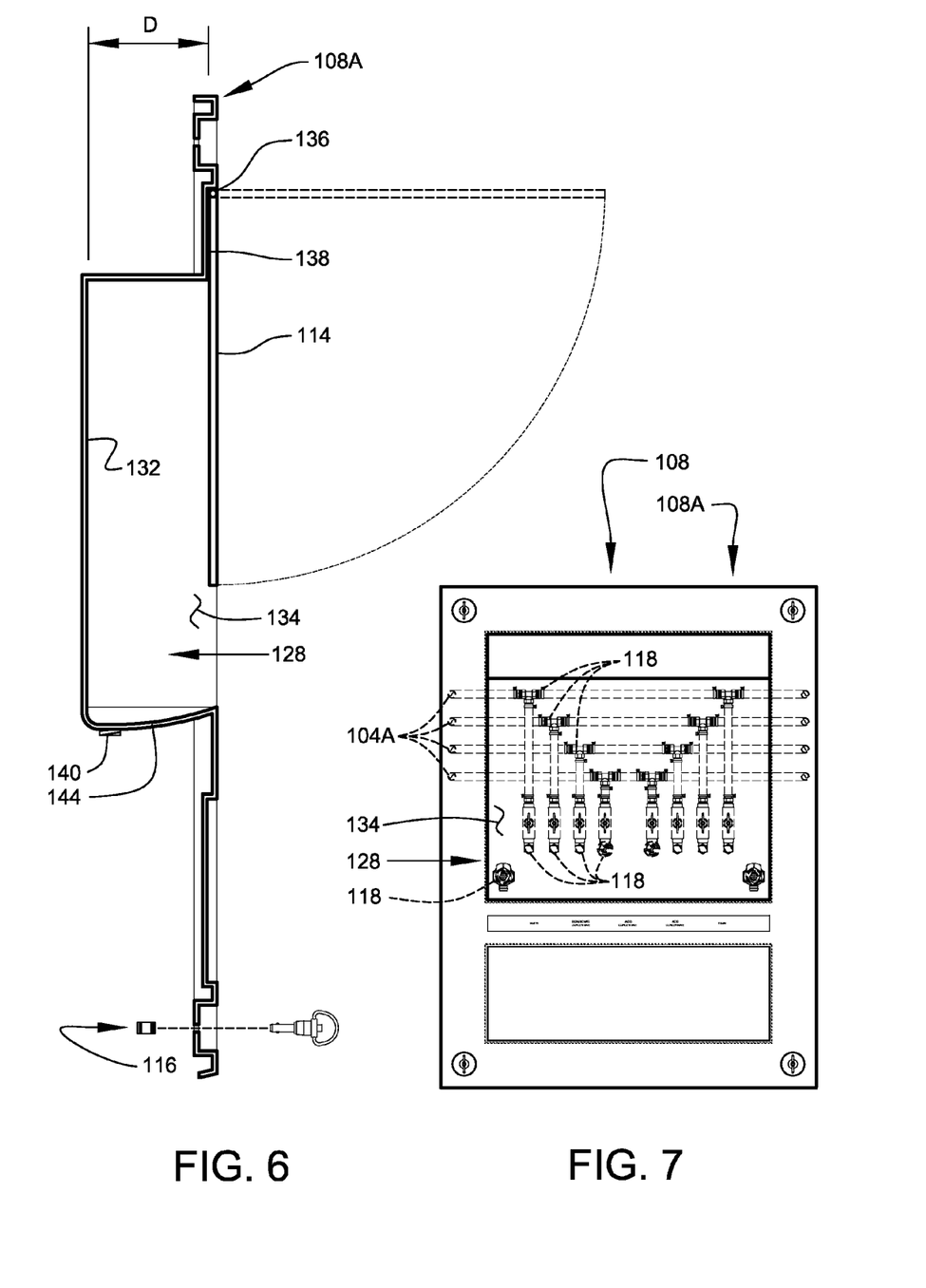
FIG. 6 shows a sectional view taken, through the section 6-6 of FIG. 5, according to the preferred embodiment of FIG. 1.
FIG. 7 shows a front elevational view, illustrating a plumbing consolidation panel, according to the preferred embodiment of FIG. 1.

FIG. 7 shows a front elevational view, illustrating plumbing consolidation panel 108A, according to the preferred embodiment of FIG. 1. Present-day kidney-dialysis machines commonly require multiple fluid-transfer elements 104A, including, an external source of treated water, acid and bicarbonate concentrates, dialysate, and a means for waste-fluid disposal. Such fluid-transfer elements 104A preferably comprise valves, pipe couplers, and similar apparatus, as diagrammatically illustrated in FIG. 7. Those of ordinary skill in the art of plumbing installations will appreciate that any of the above-noted plumbing fittings are a potential source of fluid leaks. It is often of critical importance that the fluids not be allowed to collect within the chase enclosure, should a leak develop. It is well established that such leakages promote the development of mold, may produce other health risks associated with the presence of persistent moisture, and can cause costly damage to the affected building components.

Consolidation panel 108A is preferably designed to mitigate problems associated with fluid leaks that will inevitably occur during use preferably by locating most, if not all, pipe terminations and termination fittings 118 (comprising valves, pipe couplers, etc.) within fluid collector 128.

Figure 8:
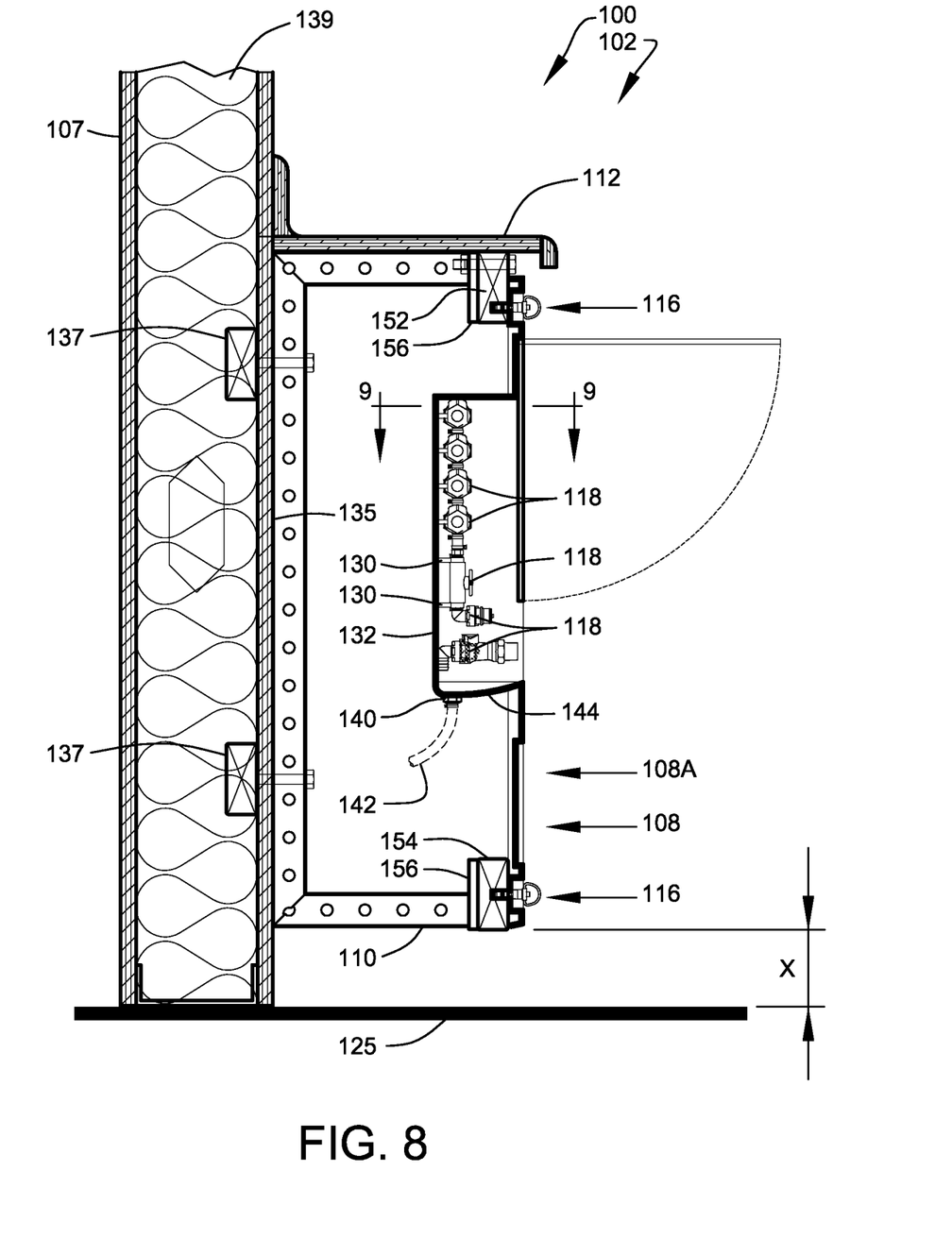
FIG. 8 shows a sectional view taken, through the section 8-8 of FIG. 4, according to the preferred embodiment of FIG. 1.
Figures 9, 10:
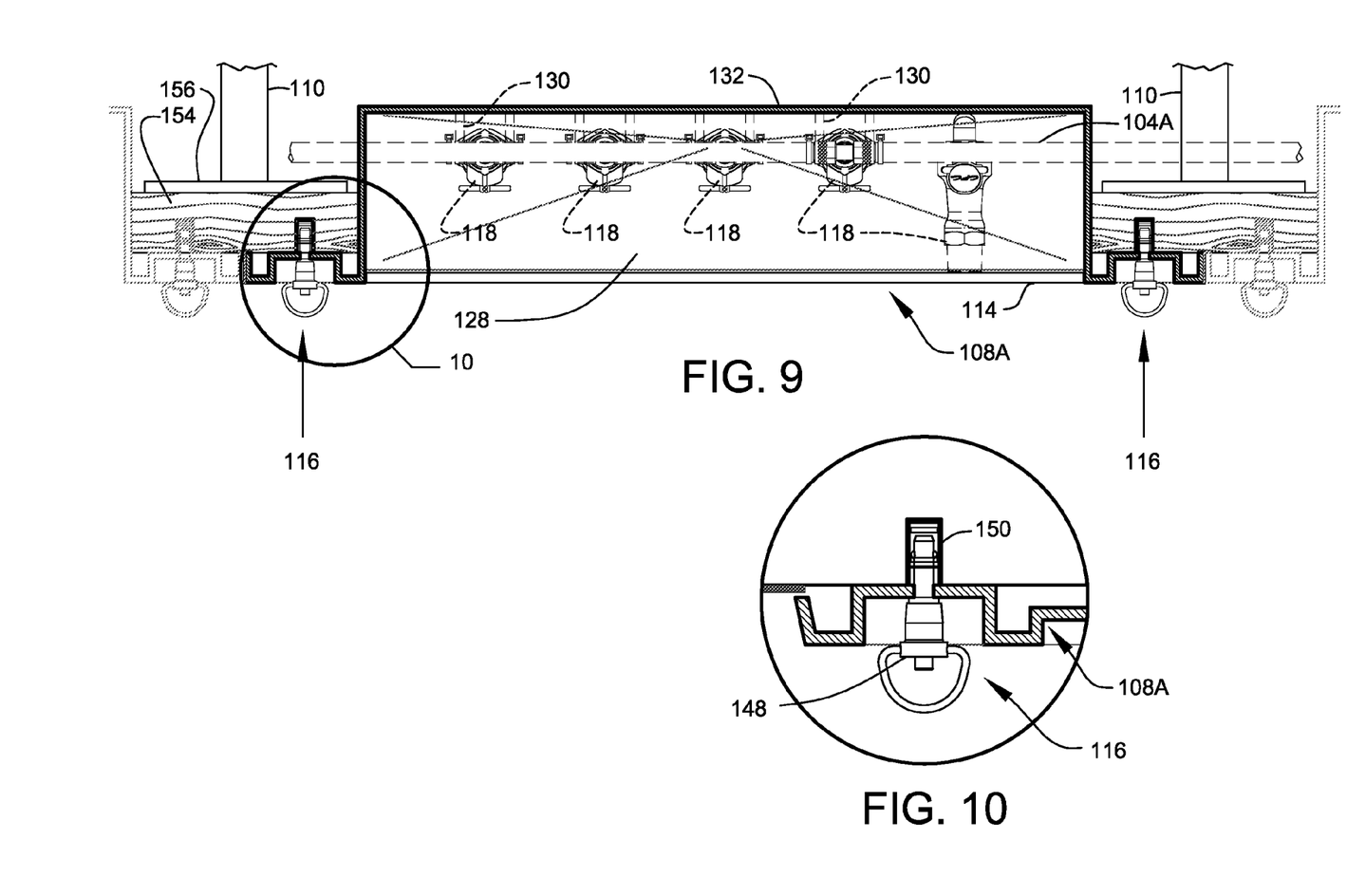
FIG. 9 shows a sectional view taken, through the section 9-9 of FIG. 8, according to the preferred embodiment of FIG. 1.
FIG. 10 shows a sectional view, enlarged for clarity, of the detail 10 of FIG. 9.

FIG. 8 shows a sectional view taken, through the section 8-8 of FIG. 4, according to the preferred embodiment of FIG. 1. FIG. 9 shows a sectional view taken, through the section 9-9 of FIG. 8. In preferred installations utilizing modular wall-chase 102, an attempt is made to route the fluid transfer lines extending within modular wall-chase 102 in continuous unbroken runs between their sources and the consolidation panels 108A that preferably function as the points of attachment for the dialysis machines. In such installations, an attempt is also made to locate any and all pipe terminations and termination fittings 118, which represent the most likely points of fluid leakage, fully within fluid collector 128 (at least embodying herein fluid collecting means for collecting at least one discharged fluids), as shown. Consolidation panels 108A are preferably configured to assist in establishing such a preferred fluid-collecting and containment arrangement, in part, by providing a containment area having a physical volume capable of holding all pipe terminations and termination fittings 118 required for supporting dialysis-machine operations.

In the preferred embodiments of the system, fluid collector 128 of consolidation panel 108A is capable of holding three or more industry-standard shut-off valves, such as, for example, PVC ball valves, ½-inch NPT male supply inlet valves, ¾-inch NPSH male hose outlet valves, etc. FIG. 7 demonstrates the ability of fluid collector 128 to accommodate at least eight PVC ½-inch ball valves, eight PEX (cross-linked polyethylene)-compatible ½-inch tee connectors, and two HFC12-series quick-connect fittings for ½-inch PEX waste lines.

Preferably, termination fittings 118 are firmly positioned within fluid collector 128, preferably using sets of polymer-compatible support tabs 130, which are preferably joined with respective termination fittings 118, and are subsequently solvent welded to the rear wall 132 of fluid collector 128, as shown (at least embodying herein at least one connection positioner structured and arranged to position, in a fluid-collecting arrangement with respect to such at least one fluid collector, at least three termination connections of the first set of fluid-transfer elements). The preferred use of such solvent-welded polymer-compatible support tabs 130 permits an installer of termination fittings 118 to fine-tune adjust the final positions of the fittings within fluid collector 128, as required. Upon reading this specification, those with ordinary skill in the art will now appreciate that, under appropriate circumstances, considering such issues as design preference, user preferences, marketing preferences, cost, structural requirements, available materials, technological advances, etc., other positioning arrangements such as, for example, mechanical fastened holders, brackets, pre-formed engagers, etc., may suffice.

When assembled for use, fluid collector 128 assists capture of fluids discharged from any one of the pipe terminations/termination fittings 118. To assist the management of larger volumes of fluids, fluid collector 128 preferably comprises at least one fluid-drain coupler 140 to permit the coupling of fluid collector 128 to at least one fluid-drain line 142 of service elements 104, as shown. Preferably, the base portion 144 of fluid collector 128 forms a shallow basin that preferably slopes downwardly toward fluid-drain coupler 140, as shown.

Fluid collector 128 is preferably arranged, within the front of plumbing consolidation panel 108A, so as to provide a large access opening 134 to the interior cavity of fluid collector 128. This preferred arrangement enables direct user access to each one of the termination fittings 118 located therein, preferably without demounting or repositioning plumbing consolidation panel 108A from the support frames 110 (at least embodying herein at least one termination-connection access structured and arranged to enable physical access to each one of the at least three termination connections without repositioning of such at least one consolidator panel from at least one mounted position with respect to such at least one surface; and, at least embodying herein termination-connection accessing means for enabling physical access to each one of the at least three termination connections without repositioning of such consolidating means from at least one mounted position with respect to such at least one surface).

Plumbing consolidation panel 108A (at least embodying herein at least one first consolidator panel structured and arranged to consolidate at least a set of fluid-transfer elements of the local building services; and, at least embodying herein first consolidating means for consolidating at least a set of fluid-transfer elements of the local building services) preferably includes at least one removable cover panel 114, as shown, which is preferably configured to at least partially cover the installed termination fittings 118 (at least embodying herein at least one termination-connection cover structured and arranged to be positionable to at least partially cover the at least three termination connections when the at least three termination connections are positioned in the fluid-collecting arrangement with respect to such at least one fluid collector, wherein such at least one termination-connection cover comprises at least one removable retainer structured and arranged to removably retain such at least one termination-connection cover in the position at least partially covering the at least three termination connections). Cover panel 114 is preferably designed to be easily relocated to provide quick access to the underlying termination fittings 118, as required. In one preferred arrangement of the system, the upper portion of cover panel 114 is pivotally coupled to plumbing consolidation panel 108A, preferably using pivot assembly 136, as shown, so that the cover can be lifted and rotated up and away from access opening 134. In this preferred arrangement, cover panel 114 is preferably secured in place using one or more magnetic couplers 138. Upon reading this specification, those with ordinary skill in the art will now appreciate that, under appropriate circumstances, considering such issues as design preference, user preferences, marketing preferences, cost, structural requirements, available materials, technological advances, etc., other cover arrangements such as, for example, utilizing a cover panel having openings to permit users to directly access the valve control handles, providing a lower closure panel to further enclose termination fittings, etc., may suffice.

Referring again to the front view of FIG. 5, plumbing consolidation panel 108A preferably comprises at least one accommodation for placement of label indicia 115, as shown. Such label indicia 115 is preferably applied to the outer face of plumbing consolidation panel 108A and preferably functions to identify the positions of the fluid supply connections located within fluid collector 128.

FIG. 10 shows a sectional view, enlarged for clarity, of the detail 10 of FIG. 9 illustrating a preferred quick-release fastener 116 used to secure preformed consolidator panel 108 to a portion of support frame 110. Referring to both FIG. 9 and FIG. 10, preferably, each preformed consolidator panel 108 is secured to a portion of support frame 110 utilizing a set of four quick-release fasteners 116, as shown (at least embodying herein at least one releasable coupler structured and arranged to releasably couple a respective one of such at least one first consolidator panel and such at least one second consolidator panel to such at least one portion of such at least one support frame; and, at least embodying herein removable mounting means for assisting removable mounting of such first consolidating means to at least one surface of the at least one treatment facility). In one preferred arrangement of the system, each quick-release fastener 116 is preferably designed to be hand operable and releasable without the use of tools. In one preferred arrangement, each quick-release fasteners 116 preferably comprises a quarter-turn locking pin 148 designed to releasably engage socket assembly 150. Socket assemblies 150 are preferably integrated within support frames 110, as shown. In this preferred arrangement, the upper socket assemblies 150 are preferably embedded within a continuous top rail 152 of support frame 110, with the lower socket assemblies 150 preferably embedded within a continuous bottom rail 154 of support frames 110, as shown. Preferably, top rail 152 and bottom rail 154 are mechanically affixed to a respective mounting member 156 of support frames 110, as shown. Preferably, both top rail 152 and bottom rail 154 comprise plywood. Alternately preferably, both top rail 152 and bottom rail 154 comprise a two inch by four inch synthetic composite lumber product, such as, for example, a composite wood material consisting of recycled plastic and reclaimed wood. Upon reading this specification, those with ordinary skill in the art will now appreciate that, under appropriate circumstances, considering such issues as design preference, user preferences, marketing preferences, cost, structural requirements, available materials, technological advances, etc., other mounting arrangements such as, for example, the use of alternate mounting brackets, other Dzus-type quick-release fasteners, friction-based engagements, tab-and-socket engagements, etc., may suffice.

The preferred installation of FIG. 8 results in the suspension of modular wall-chase 102 above floor surface 125, as shown. This preferred arrangement is achieved by mounting the preassembled support frames 110 to wall 107 at an elevation placing bottom edge 122 of the preformed consolidator panels 108 a distance X above floor surface 125, as shown. In one preferred arrangement of the system, distance X comprises a clear height of about six inches.

It is noted that the preferred installation of FIG. 8 utilizes a rigid substrate to form the back wall 135 of the chase. In one preferred embodiment of the system, back wall 135 preferably comprises a plywood substrate having a nominal thickness of about ¾ inch. The plywood substrate preferably extends from floor surface 125 upwardly to terminate at least above the mounted support frames 110. The chase-exposed side of the plywood substrate preferably comprises at least one water-resistant finish with an epoxy paint finish being most preferred.

Each support frames 110 is preferably mounted to wall 107 using mechanical fasteners, preferably comprising a set of lag screws extending through the plywood substrate into horizontal blocking members 137 located between stud members 139 of wall 107.

Figure 11:
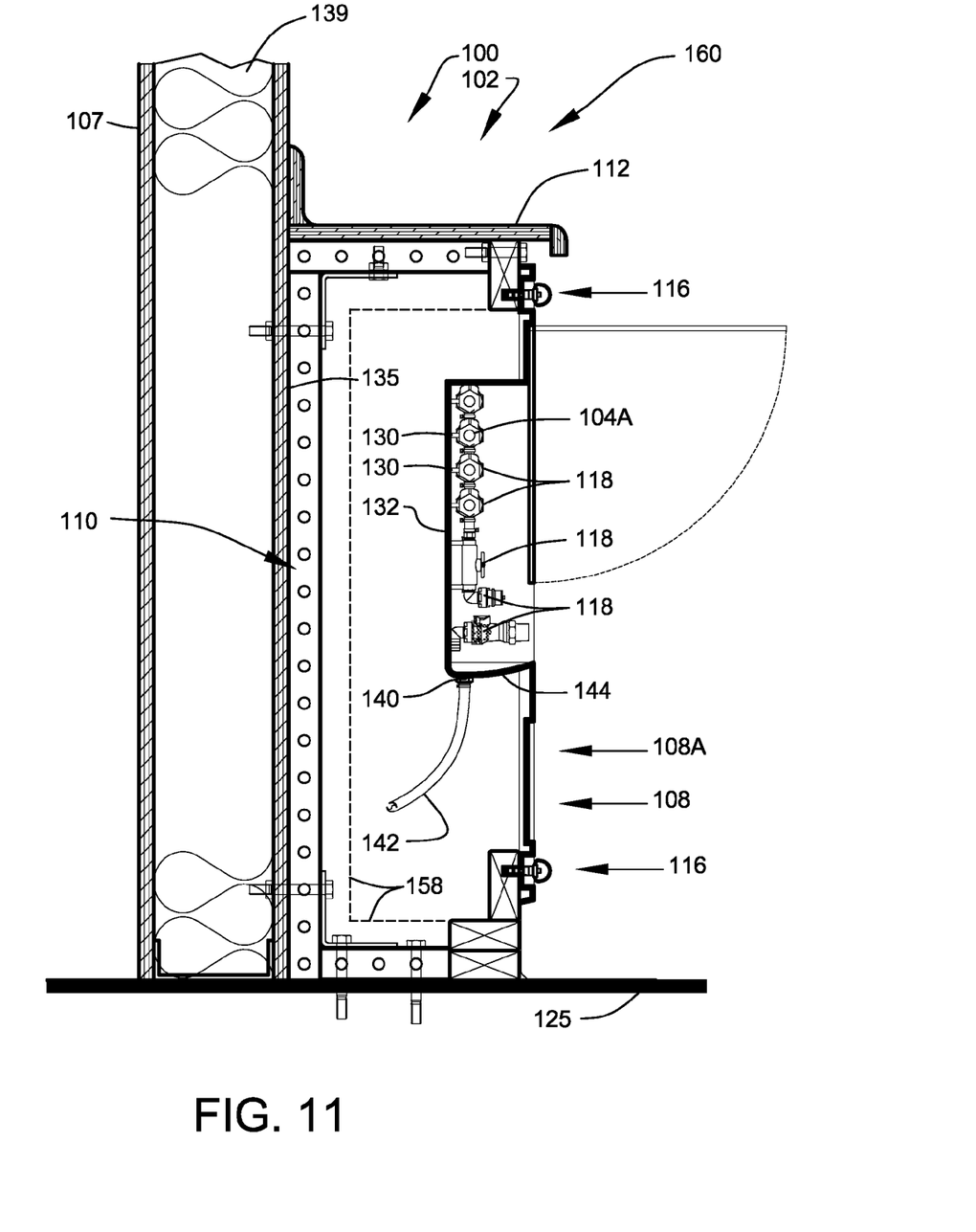
FIG. 11 shows an alternate sectional view, taken through a line of section similar to section 8-8 of FIG. 4, illustrating a floor-mounted chase arrangement, according to another preferred embodiment of the present invention.

FIG. 11 shows an alternate sectional view, taken through a line of section similar to section 8-8 of FIG. 4, illustrating floor-mounted chase arrangement 160, according to another preferred embodiment of the present invention. In the preferred installation of FIG. 11, modular wall-chase 102 is preferably supported from both wall 107 and floor surface 125, as shown. This preferred arrangement is achieved by mounting the preassembled support frames 110 to wall 107 and floor surface 125. As diagrammatically illustrated in FIG. 11, support frames 110 may preferably be constructed principally from steel channel, as shown. Alternately preferably, may be constructed from principally from nominal two inch by four inch (2×4) synthetic composite lumber products, such as, for example, a composite wood material 158 consisting of recycled plastic and reclaimed wood (as diagrammatically indicated by the dashed-line depiction).

Figure 12:
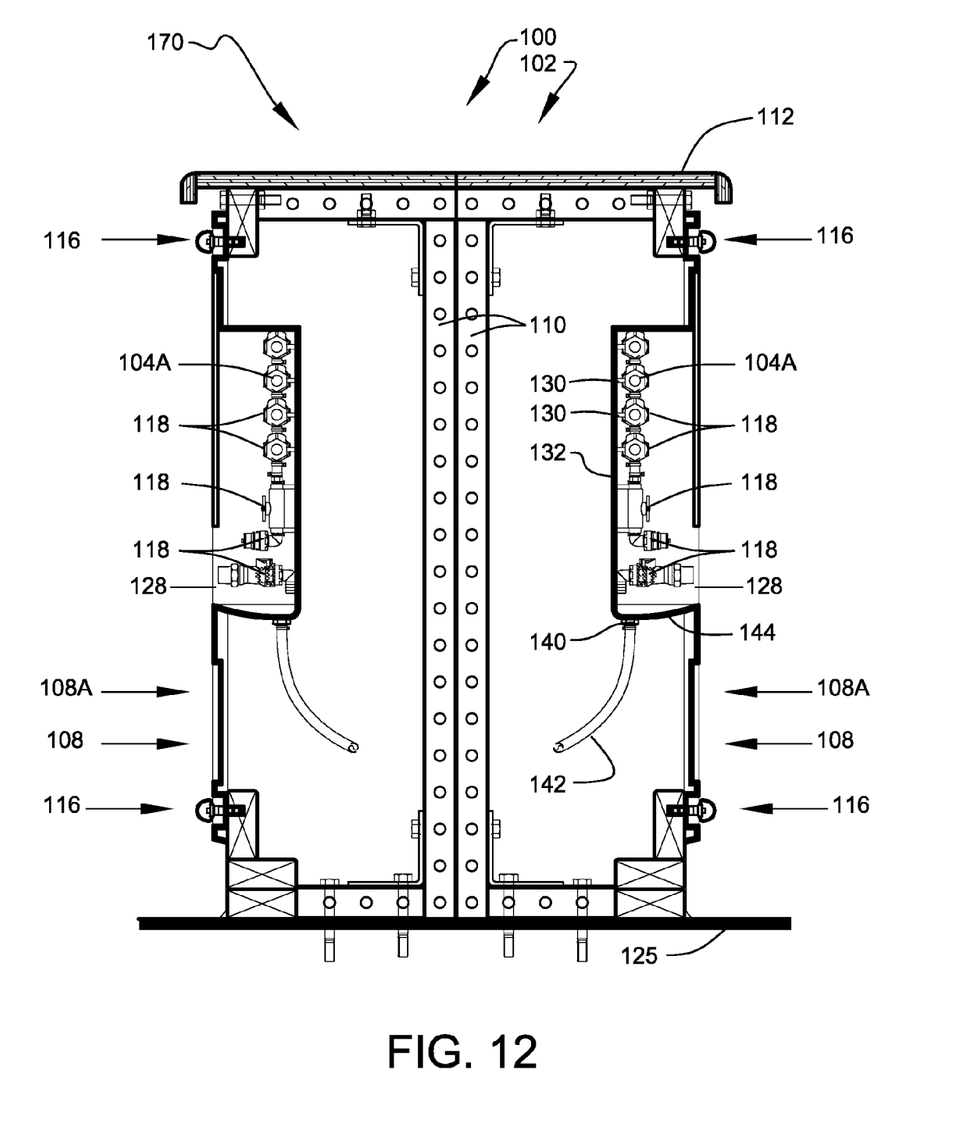
FIG. 12 shows an alternate sectional view, taken through a line of section similar to section 8-8 of FIG. 4, illustrating a back-to-back chase arrangement, according to another preferred embodiment of the present invention.

FIG. 12 shows an alternate sectional view, taken through a line of section similar to section 8-8 of FIG. 4, illustrating a back-to-back chase arrangement 170, according to another preferred embodiment of the present invention. In the preferred installation of FIG. 12, a double modular wall-chase 102 is preferably supported from floor surface 125, as shown. This preferred arrangement is achieved by mounting two preassembled support frames 110 back-to-back, as shown. The finishing millwork top 112 is preferably sized to span the full width of both support frames 110, as shown.

Each of the above-described embodiments of modular wall-chase 102 preferably comprises an upper substantially horizontal work surface, as shown. As previously noted, such work surfaces are preferably formed by the mounting of a millwork top 112 to support frame 110. In general, preferred millwork tops 112 comprise non-porous surfaces that repel liquids to inhibit growth of bacteria, mold, and mildew. Furthermore, preferred millwork tops 112 comprise good chemical and wear resistance. Millwork tops 112 preferably comprise one of a number of industry-standard millwork constructions, such as, for example, plastic laminate tops, solid-surface materials, stainless steel tops, etc.

Plastic laminate materials suitable for use as millwork top 112 include products distributed under the Chemsurf® brand by Wilsonart of Temple, Tex. Solid surface materials suitable for use as millwork top 112 include acrylic solid-surface products distributed under the Meganite™ brand name by Meganite Inc. of Pomona, Calif. Upon reading this specification, those with ordinary skill in the art will now appreciate that, under appropriate circumstances, considering such issues as design preference, user preferences, marketing preferences, cost, structural requirements, available materials, technological advances, etc., other work surface materials such as, for example, alternate polymer composites, natural and recycled materials, providing pre-formed consolidation panels that incorporate an upper horizontal surface, etc., may suffice.

FIG. 13 shows a perspective view, illustrating multipurpose panel 108B, according to the preferred embodiment of FIG. 1. FIG. 14 shows a front elevational view, further illustrating the modular multipurpose panel 108B of FIG. 13. Multipurpose panels 108B preferably comprise an undifferentiated (blank) front panel 172, as shown. Multipurpose panels 108B are most frequently used as a blank cover for portions of the underlying support frames 110 (see FIG. 2) and as a means for consolidating and supporting electrical-supply elements 104B and data elements 104C, as shown in FIG. 1, FIG. 2, and FIG. 4. The undifferentiated front panel 172 is preferably design to accommodate any number of custom electrical-supply elements 104B and/or data elements 104C by factory or field modification. Preferably, each multipurpose panel 108B is secured to the support frames 110 utilizing a set of four quick-release fasteners 116, as shown. The above-described arrangements at least embody herein at least one second consolidator panel structured and arranged to consolidate at least a set of electrical-supply elements of the local building services, wherein such at least one second consolidator panel comprises such at least one removable mount structured and arranged to assist removable mounting of such at least one second consolidator panel to the at least one surface of the at least one treatment facility, and wherein such at least one second consolidator panel is further structured and arranged to physically conform to at least one modularized format. Upon reading this specification, those with ordinary skill in the art will now appreciate that, under appropriate circumstances, considering such issues as design preference, marketing preferences, cost, structural requirements, available materials, technological advances, etc., other panel arrangements such as, for example, providing panels pre-formed to receive electrical and/or data components, providing panels at least some electrical and/or data components preinstalled, etc., may suffice.

Furthermore, upon reading this specification, those with ordinary skill in the art will now appreciate that, under appropriate circumstances, considering such issues as design preference, user preferences, marketing preferences, cost, structural requirements, available materials, technological advances, etc., other system arrangements such as, for example, pre-installing or integrating at least a portion of the required plumbing elements within one or more of the chase components, pre-installing or integrating electrical elements within other chase components, etc., may suffice.

Figure 15:
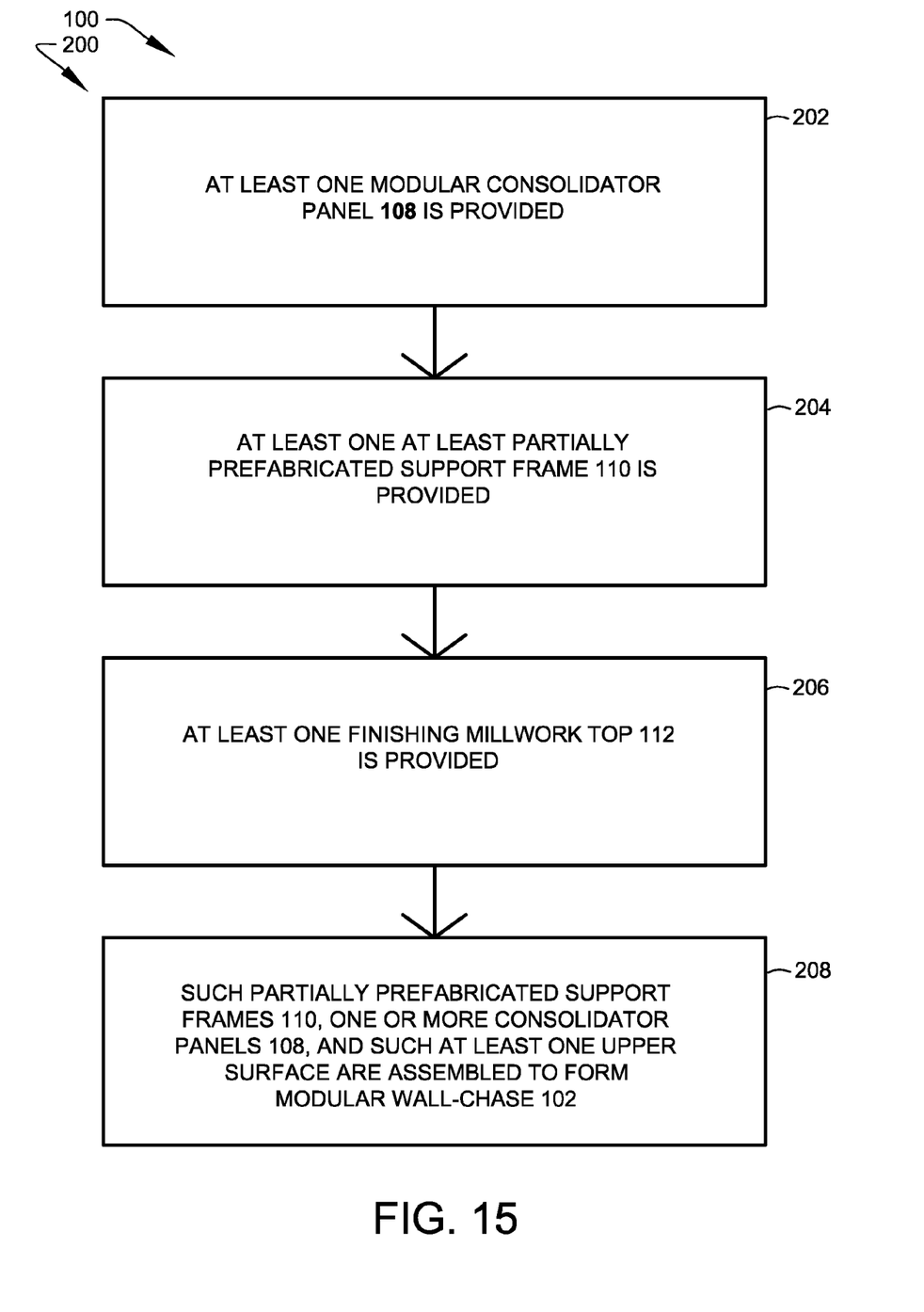
FIG. 15 shows a flow diagram illustrating a preferred method of assembling, within the kidney dialysis facility, at least one dialysis-services chase that, when assembled, provides at least partially concealed routing of local building services associated with the operation of the kidney dialysis machines.

FIG. 15 shows a flow diagram illustrating preferred method 200 of assembling, within kidney dialysis facility 105, modular wall-chase 102 that, when assembled, provides at least partially concealed routing of local building services associated with the operation of kidney-dialysis machines 103.

In initial preferred step 202 of method 200, at least one modular consolidator panel 108 is provided. Such modular consolidator panels 108 preferably comprises one or more of either plumbing consolidation panel 108A (at least embodying herein a first consolidator panel) or multipurpose panel 108B (at least embodying herein a second consolidator panel). It is noted that step 202 may comprise a concurrent providing of both plumbing consolidation panels 108A and multipurpose panels 108B. As previously described, the preformed consolidator panels 108 preferably conform to a defined modular format.

Next, as indicated in preferred step 204, at least one at least partially prefabricated support frame 110 is provided. Such support frames 110 are preferably provided in pairs and are preferably structured and arrange to support at least one of the above consolidator panels 108.

Next, as indicated in preferred step 206, at least one finishing millwork top 112 (i.e., at least one upper surface) is provided. Finishing millwork top 112 is preferably configured to provide at least partial upper surface covering of the support frames 110. Next, as indicated in preferred step 208, such partially prefabricated support frames 110, one or more consolidator panels 108, and such at least one upper surface are assembled to form modular wall-chase 102.

Thus, as indicated in the above-preferred steps of method 200, modularized assembly of such modular wall-chase 102, providing at least partially concealed routing of the local building services associated with the operation of kidney-dialysis machines 103, is preferably assisted.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. A dialysis support system in a treatment facility for use with at least one hemodialysis machine in the facility, said support system designed to be mounted to a vertically oriented wall (107) of a building or facility comprising
    (a) a hollow housing (110) mounted on and extending outwardly from said wall (107) and including a
        (i) back (135), and
        (ii) forward portion (152, 154) spaced apart from said back (135) and said wall (107);
    (b) a consolidator panel (108) mounted on said forward portion (152, 154) of said hollow housing (110) and including
        (i) an interior cavity
            extending inwardly into said housing (110) and toward and spaced apart from said back (135) and said wall (107), and
            having vertically oriented sides;
        (ii) a vertically oriented wall (132) at the rear of said interior cavity,
        (iii) a fluid collector (128) including
            an opening (134) to access said interior cavity,
            a horizontally oriented basin (144) partially bounding said interior cavity,
            a fluid-drain line (142) connected to said basin (144);
    (c) a plurality of horizontally oriented generally parallel non-terminating primary fluid transfer feeder lines (104A) extending inside said housing (110) and completely in and through said interior cavity from one side to the other side of said interior cavity;
    (d) a plurality of terminating generally parallel vertically oriented supplementary fluid transfer feeder lines each
        (i) located completely inside said housing (110) and in said interior cavity,
        (ii) extending outwardly from said primary fluid transfer feeder lines (104A), and,
        (iii) having a first and second terminating ends;
    (e) a plurality of connector fittings (118) each
        (i) located completely in said interior cavity and said housing (110),
        (ii) integrated in one of said primary fluid transfer feeder lines,
        (iii) connected to said first terminating end of a different one of said supplementary fluid transfer feeder lines to permit fluid to flow from said one of said primary fluid transfer lines and comprising into said one of said supplementary fluid transfer lines;
        (iv) a clustered array of adjacent valves (118) each completely in said interior cavity and said housing (110) and connected to said second terminating end of a different one of said supplementary fluid transfer feeder lines;
    said primary and supplementary fluid transfer feeder lines, said connector fittings, and
    said valves each being positioned directly above said basin (144).

* * * * *